US012766214B2

(12) United States Patent
Lunman, II et al.

(10) Patent No.: US 12,766,214 B2
(45) Date of Patent: Oct. 20, 2026

(54) CONTINUOUS DISINFECTION DEVICE

(71) Applicants: Kyler F. Lunman, II, Fernandina Beach, FL (US); Richard A. Ferdinand, Old Tappan, NJ (US)

(72) Inventors: Kyler F. Lunman, II, Fernandina Beach, FL (US); Richard A. Ferdinand, Old Tappan, NJ (US)

(73) Assignee: Bio1Defense, Corp., Old Tappan, NJ (US)

( * ) Notice: Subject to any disclaimer, the term of this patent is extended or adjusted under 35 U.S.C. 154(b) by 330 days.

(21) Appl. No.: 18/290,768

(22) PCT Filed: Jul. 23, 2022

(86) PCT No.: PCT/US2022/038100
§ 371 (c)(1),
(2) Date: Jan. 20, 2024

(87) PCT Pub. No.: WO2023/004176
PCT Pub. Date: Jan. 26, 2023

(65) Prior Publication Data

US 2025/0090713 A1 Mar. 20, 2025

Related U.S. Application Data

(60) Provisional application No. 63/225,041, filed on Jul. 23, 2021.

(51) Int. Cl.
*A61L 9/20* (2006.01)
*F24F 8/22* (2021.01)

(52) U.S. Cl.
CPC .................. *A61L 9/20* (2013.01); *F24F 8/22* (2021.01); *A61L 2209/12* (2013.01); *A61L 2209/14* (2013.01)

(58) Field of Classification Search
CPC .... A61L 9/20; A61L 2209/12; A61L 2209/14; F24F 8/22
See application file for complete search history.

(56) References Cited

U.S. PATENT DOCUMENTS 4,990,313 A 2/1991 Pacosz
5,112,370 A 5/1992 Gazzano
(Continued)

FOREIGN PATENT DOCUMENTS

CN 2725759 Y 9/2005
DE 102020119540 A1 1/2022
(Continued)

OTHER PUBLICATIONS

International Search Report and Written Opinion for International application No. PCT/US2022/038100 from the European Patent Office completed Nov. 25, 2022.
(Continued)

*Primary Examiner* — David E Smith
(74) *Attorney, Agent, or Firm* — Keusey & Associates, P.C.

(57) ABSTRACT

A continuous disinfection device for removing pathogens from an airspace including a housing having an air intake and output and containing a treatment chamber. The treatment chamber has inner boundary walls protectively surrounding a source of ultraviolet (UVC) irradiance and an internal volume measured on a basis of a unit size of 1 cubic foot. An air flow management system between the inner boundary walls and the UVC source provides an exposure slot having a cross-sectional area receiving at least 20 kWatts/m2. A fan draws air through the treatment chamber. The cross-sectional area of the exposure slot provides all drawn air with at least 360 milliseconds of dwell time within the exposure slot to produce treated air with at least 99.99% of pathogens eradicated while maintaining a throughput of
(Continued)

about 120 units of air per minute drawn through the pathogen removal system.

19 Claims, 3 Drawing Sheets

(56) References Cited

U.S. PATENT DOCUMENTS

| | | | |
|---|---|---|---|
| 5,558,158 | A | 9/1996 | Elmore |
| 5,752,878 | A | 5/1998 | Balkany |
| 5,817,276 | A | 10/1998 | Fencl |
| 7,993,580 | B2 | 8/2011 | Anderle et al. |
| 8,986,607 | B2 | 3/2015 | Anderle et al. |
| 9,150,619 | B2 | 10/2015 | Edwards et al. |
| 9,310,088 | B2 | 4/2016 | Melikov |
| 9,675,726 | B2 | 6/2017 | Lunman |
| 10,376,604 | B2 | 8/2019 | Romo et al. |
| 10,946,321 | B1 | 3/2021 | Hamidzai |
| 10,987,440 | B1 | 4/2021 | Sood |
| 11,224,675 | B1 | 1/2022 | Akeasu |
| 2004/0211321 | A1 * | 10/2004 | Gibson .................... A61L 9/20 96/381 |
| 2006/0045796 | A1 | 3/2006 | Anderle |
| 2008/0152548 | A1 * | 6/2008 | Clark ...................... A61L 9/205 422/121 |
| 2010/0254852 | A1 * | 10/2010 | Metteer .................. B01D 53/75 422/4 |
| 2012/0156094 | A1 | 6/2012 | Gordon |
| 2012/0199003 | A1 | 8/2012 | Melikov |
| 2018/0021471 | A1 | 1/2018 | Kronsney |
| 2018/0169279 | A1 | 6/2018 | Randers-Pehrson |
| 2019/0160305 | A1 | 5/2019 | Randers-Pehrson |
| 2019/0216970 | A1 | 7/2019 | Eide |
| 2020/0016286 | A1 | 1/2020 | Clack |
| 2021/0010692 | A1 | 1/2021 | Worrilow |
| 2021/0128713 | A1 | 5/2021 | Tobin |
| 2021/0356153 | A1 | 11/2021 | Nesler |
| 2021/0379233 | A1 | 12/2021 | Banaei et al. |
| 2022/0008604 | A1 | 1/2022 | Carlos, Jr. |
| 2022/0054697 | A1 * | 2/2022 | Spittler ..................... A61L 9/20 |

FOREIGN PATENT DOCUMENTS

| | | | |
|---|---|---|---|
| EP | 3943125 | A1 | 1/2022 |
| WO | 2016196904 | A1 | 12/2016 |
| WO | 2021084237 | A2 | 5/2021 |

OTHER PUBLICATIONS

International Search Report and Written Opinion for International application No. PCT/US2022/80203 from the European Patent Office completed Jan. 17, 2023.

* cited by examiner

CONTINUOUS DISINFECTION DEVICE

BACKGROUND OF THE INVENTION

1. Field of the Invention

The invention relates to a continuous disinfection device and related methods.

2. The Prior Art

With the occurrence of the Covid-19 pandemic, there is an increased interest in air disinfection systems that can be readily deployed, easily maintained and have very high effectiveness exceeding 99%.

There are generally four main types of UV air treatment. A first type comprises airstream disinfection via in-duct and/or air handling units in the HVAC system. A second type includes Recirculation units (free standing) that consist of ultraviolet light (UV) lamps and fixtures in a housing. A third type includes Upper-Room Systems which consist of multiple UV lamps hung from the ceiling or walls which are shrouded from the people below because humans cannot tolerate direct exposure to UVC. Finally, a fourth type comprises Barrier Systems which are normally hung in the overhead portion of the door with louvers to constrain the UVC rays.

However, these types of UV air treatment have drawbacks which limit their application. Recirculation units are comparatively smaller and normally sit in a corner of a room or area thereby treating very small areas. Upper room and Barrier types normally have no ability to control or direct airflow either to or away from their unit. In many of these systems the areas have to be evacuated for them to be utilized. Additionally, these UV air treatment types are not scalable so they are unable to irradiate airborne and surface pathogens in different sized areas or airspaces.

One approach is detailed in our prior U.S. Pat. No. 9,675,726 entitled Scalable Airborne Pathogen Removal System which describes an air handling system where circulated air is exposed to ultraviolet light. However, recent discoveries in immunology and social health management require a more robust system with increased effectiveness.

Therefore, a need exists for novel systems and methods configured for the irradiation of airborne and surface pathogens using ultraviolet light. There also exists a need for novel ultraviolet germicidal irradiation (UVGI) airborne pathogen removal air movement systems which can be installed anywhere. Finally, there exists a need for novel scalable ultraviolet germicidal irradiation airborne pathogen removal air movement systems.

Furthermore, implementation of the present invention, with or without the prior known air-handling methods, may include a multiplicity of new sequences and cycles that disable, kill, eradicate and/or interdict (slow, deter or stop) formations of infectious concentrations of disease caused by viruses, bacteria and fungi, along with many additional pollutants and contaminants.

SUMMARY OF THE INVENTION

The present invention may use various known or new air-handling methods, processes and sub systems that, when used to implement the present invention in novel ways, via application of ultraviolet germicidal irradiation (UVGI) and/or other forms of purposed energy emissions potentially including narrow and multi spectral light emissions; e-beams; avalanche dump laser light emissions, x rays, LED's and ultra sound; among others to achieve a sequence of physical events that, in whole or in part may interdict (slow, deter or stop), disable and/or kill airborne biological agents of potential infections, contagions and pandemics.

The present invention also asserts new claims to the scalability of certain sequences and power levels of same or similar known energy emitters that may also continue to be linked to air circulation and air recirculation processes that disrupt and/or prevent formation of infectious concentrations of pathogens and allergens thus generally protecting air breathing creatures. Advances of the present invention elevate the interdiction performance to a level at which the airborne spreading progress of a contagion among humans can be stopped within a protected indoor space of the invention. Each "stopped" location is thereby eliminated as a possible disease super spreader node in a contagious network. Furthermore each "stopped" location becomes a potential herd immunity microcell.

Furthermore, implementation of the present invention, with or without the prior known air-handling methods, may include a multiplicity of new sequences and cycles that disable, kill, eradicate and/or interdict (slow, deter or stop) formations of infectious concentrations of disease caused by viruses, bacteria and fungi, along with many additional pollutants and contaminants.

These and other related objects are achieved according to an embodiment of the invention of a continuous disinfection device for removing pathogens from an airspace. The system includes a housing having an air intake and an air output. Housing contains a treatment chamber having inner boundary walls protectively surrounding a source of ultraviolet (UVC) irradiance within said housing and having a volume within the boundary walls measured on a basis of a unit size of 1 cubic foot. An air flow management system is located between the inner boundary walls and the source of ultraviolet irradiance to provide an exposure slot having a cross-sectional area receiving at least 20 kWatts/m2. An air motivator, like a fan or blower, is configured to draw air from the airspace into the air intake through the treatment chamber in a downstream direction and expel treated air out of the air output back to the airspace. The cross-sectional area of the exposure slot is configured and dimensioned to provide all drawn air with at least 360 milliseconds of dwell time within the exposure slot to produce treated air with at least 99.99% of pathogens eradicated while maintaining a throughput of about 120 units of air per minute drawn into and expelled out of the pathogen removal system.

The treatment chamber includes an X-Y central plane where air passes through the treatment chamber in a downstream X direction. The passing air encounters the air flow management system that varies in height as measured in a Z direction perpendicular to the X-Y central plane to induce turbulence characterized by a high Reynolds number so that clumping, grouping, tailing, trailing and shadowing is avoided to maximize pathogen eradication. The air flow management system includes a ramp section that originates upstream from the source of irradiance spaced from the inner boundary wall and slopes toward the inner boundary wall. The ramp section is closest to the inner boundary wall at a location that is downstream of the source of ultraviolet irradiance. The air flow management system further includes a gate section with a terminal end which narrows the cross-sectional area of the treatment chamber by 40 to 60 percent to direct a randomized air flow away from the inner boundary wall toward the source of ultraviolet irradiance.

The source of ultraviolet irradiance between 20-35 kWatts/m2 across the entirety of the exposure slot. The source of ultraviolet irradiance is selected from a longitudinally-extending ultraviolet lamp, bulb, or LED that generates oriented parallel to the terminal end of the gate section through 95-100% of the treatment chamber emitting irradiance in the range of 253.7 and 275 nm, inclusive. The gate section extends away from the inner boundary wall in a generally perpendicular direction and creates a choke point that increases the velocity of air passing through the choke point according to the Bernoulli Principle. The gate section and the ramp section are formed from a continuous ribbon having a reflectivity of at least 80%. The UVC bulb and the reflectivity of the continuous ribbon are selected to provide between 20-35 kWatts/m2, on average, across the entirety of the exposure slot. The ramp section smoothly curves as it transitions in to the gate section. The gate section deflects a distance equal to 10-20% of its length in the upstream direction toward the source of ultraviolet irradiance as it approaches the choke point.

The air flow management system directs air drawn in to the treatment chamber through one or more stages serially-aligned in the downstream direction. Each stage includes a symmetrically increasing cross-sectional area that extends past the source of ultraviolet irradiance followed by a symmetrical reduction in cross-sectional area of 30-70%. A contour profile of the continuous ribbon in conjunction with a filtered volume of air drawn in to the treatment chamber mechanically balances induced turbulence for extended dwell time with throughput as a function of unit size while the location and reflectivity of the continuous ribbon in conjunction with a power output and configuration of the UV source photooptically maximize the irradiance of all particles. Air entering the ramp section hugs the continuous ribbon according to the Coanda Effect; air encountering a discontinuity at an end of the gate section at the choke point becomes turbulent in the vicinity of the source of ultraviolet irradiance to increase dwell time and mixing to provide a 6 log reduction of pathogens in the exposed air.

The system includes two or more longitudinally-extending UVC lamps aligned in the Y direction and arranged parallel to each other within the X-Y plane. A continuous ribbon is provided for each source of ultraviolet irradiance, with the gate section of one ribbon coupled to the ramp section of a further ribbon. A strake is provided for each adjacent pair of longitudinally-extending UVC lamps. When two or more strakes are present, they are disposed alternately above and below the X-Y plane with each strake aligned approximately midway in the X direction between its respective pair of bulbs to further increase the air's turbulence. Each strake includes one flat side and one wing-like curved side to maximize the production of mini eddies. The system may include supplemental air intakes drawn from sources separate from the airspace freely located on any wall of the housing and replaceable air filters on all intakes to limit particulate matter, debris and foreign objects from entering the treatment chamber.

The air flow management system includes a first continuous ribbon extending partially across one of the inner boundary walls having a height above the X-Y plane measured in the +Z direction. The height of the first continuous ribbon varies in the X direction while maintaining a constant height in the Y direction. A second continuous ribbon extends partially across an opposite one of the inner boundary walls having a height measured in the −Z direction. The height of the second continuous ribbon varies in the X direction while maintaining a constant height in the Y direction. The continuous ribbon comprises a ribbed panel that extends across 80-90% of the length of one of the inner boundary walls measured in the Y direction; wherein an edge of a ribbed panel provides a discontinuity to increase the turbulence of the air flow at a side wall of the treatment chamber; wherein the continuous ribbon induces turbulence characterized by a high Reynolds number, preferably an Re of between 4,000 and 5,000.

BRIEF DESCRIPTION OF THE DRAWINGS

The advantages, nature, and various additional features of the invention will appear more fully upon consideration of the illustrative embodiments now to be described in detail in connection with accompanying drawings. In the drawings wherein like reference numerals denote similar components throughout the views.

DETAILED DESCRIPTION OF THE PREFERRED EMBODIMENTS

Figure 1:
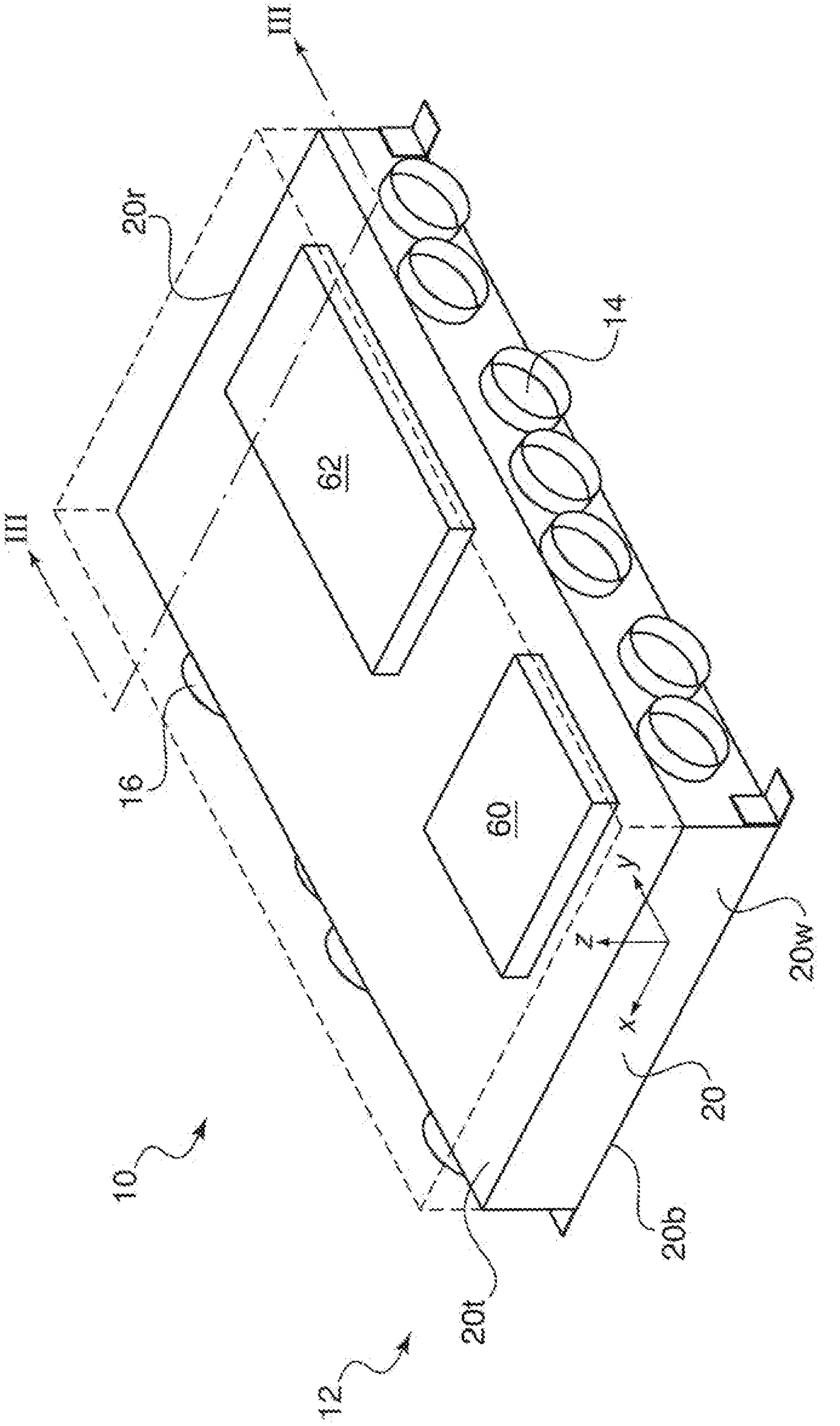
FIG. 1 is a perspective view of an embodiment of the continuous disinfection device according to the invention.

The key principle is that the device and methods according to the invention provides a unique loss of pathogenic function which leads to gains in immunity. The metrics of disinfecting microorganisms while producing antigens in real time will become a new standard in IPC-Infection Prevention and Control. Disinfecting airflow devices will deliver a continuous flow of sterile air into any type of setting-classroom, healthcare, offices-any indoor venue where people live or work.

Disinfected airflow (DA) generated by a new device, named the Continuous Disinfection Device (CDD), may be used to supply disinfected air to interior spaces and/or charge storage tanks with antigens. Disinfected air generated by the CDD may be used to continuously maintain both negative and positive pressure rooms anywhere and at any time and at substantial savings from current modalities. They may be permanent, portable and/or long- or short-term use. Also, they may service any size buildings with any number of people working and/or otherwise occupying the space. Disinfected air generated by the CDD may be used to provide large offices, commercial spaces and/or housing venues of any type and for any use all while maintaining sterile air interiors while facilitating antigen production within the space.

This new to market disinfected air production device, that will provide scalable volumes of disinfected air, while generating antigens, may be installed permanently or temporarily, in any building for any usage such as in schools or even biodefense needs at any level. A change in pathogenic DNA that results in the decreased production of a protein or a protein with impaired function indicates a loss of function. Most office and school ceiling heights are 9' to 10' high so the CDD, above, may fit in the mechanical space above the acoustical ceiling.

The CDD operates 24/7/365 and is similar to HVAC EXCEPT instead of heating and cooling the air, the CDD STERILIZES the air. This disinfection process, described elsewhere, provides over six log reductions of infectious disease-causing microorganisms such as bacteria, virus and fungi. Since the CDD operates continuously when room occupants arrive at work in the morning their offices are completely engulfed with sterile air-no disease-causing pathogens are resident.

During the day, workers are generally either sitting or standing in the breathing zone and on average will exhale 10 to 14 CFH (Cubic Feet per Hour) per employee. The CDD may generate 42,000 CFH of disinfected air (green and blue arrows). At these rates it will, to a great extent, subsume and otherwise disinfect the exhaled air of many employees/students, at the moment and on the spot. This disinfected air will provide important amounts of antigens to strengthen occupant's immune systems.

There are many unique and innovative claims to the CDD design and operation, however the most important observation is the relationship of the statistical conversation. As mentioned in the above illustration human breathing at X rates depending on their age and physical size and the CDD apparatus technology is scalable both up and down in size and volumes to fit required building sizes and populations thereof. The important observation is that any person, if infected, in any manor or stage, will exhale a small percentage of infectious pathogens within that 10 to 14 CFH of exhaled air, which are only very small quantities relative to the sum of that exhaled volume of air.

Given that the volumes of the device are scalable it may easily diffuse most any level of infectious air exhalations from any number of people simultaneously, on the spot and in the moment. All while constantly operating in real time the live operation of going on to disinfect, at overwhelming rates, newly exhaled air by the existing and/or revolving population of the conditioned area. This activity will continually maintain robust volumes of sterile air in the space, at the moment that will continue 24/7/365 that will subsume and disinfect the ongoing exhaled potentially infectious exhaled air.

In review: When the air disinfection system is operating it can deliver and maintain large amounts of resident disinfected air for any and all occupants to breathe. These amounts of disinfected air are so overwhelming that it will subsume and otherwise diffuse any amount of exhaled air that may contain infectious particles to below infectious levels. This diffused air will be continuously removed from the space, via a direct return airflow, to the system and disinfected in real time (seconds). Sterile air containing varying levels of antigens will be continuously returned into the space 24/7/365.

Potential Uses: Regional or global deployment and maintenance of the technology may reduce the potential for regional or global human infections by airborne agents of biological diseases worldwide.

Hyperlocal deployment and proper maintenance of the technology in settings such as a USA college, or a military mess hall, may also revolutionize air quality in protected indoor college and DOD spaces, as examples, to constant noninfectious levels in accordance with industry standards. The technologies may also be used to offset vaccination rejections with "passive inoculation" via normal human inhalations of antigens produced in situ via the workings of the present invention. In these cases, the disinfected breathable air contains human antigens generated by the present Invention that, when circulated and re circulated within protected spaces, may act as repeatable immune system boosters. Excess human antigens may also be passively or actively circulated throughout other spaces sharing the same HVAC systems.

Composite disinfection processes and composite in situ production of antigens and designed administration of aerosolized passive inoculations and similar processes may involve (but not necessarily be limited to) dozens of same, similar or widely-differing aggregations of airborne agents of biological pathogens and allergens wherein said aggregations may, without known numerical limits, simultaneously occupy the protected space and, without known real world limits, undergo the effects of and be changed by the systems, methods and processes of the present invention as described herein.

As a consequence, the present invention may, at any time or place, serve as a truly scalable public healthcare asset that indiscriminately, economically, safely and constantly disinfects breathable air in indoor protected spaces occupied by humans and/or other air-breathing mammals and, as a byproduct, may, via the workings of the present invention, thereby enhance human immune systems of persons within the protected spaces in multiple beneficial ways. For example, in the event that fifteen (15) different biological infectious agents are simultaneously introduced by exhaling humans into the circulating and re circulating protected indoor atmosphere of a DOD mess hall or a main college dining room or cafeteria serving one thousand (1,000) persons, then it will be likely that up to fifteen thousand (15,000) cases of new biological infection may be interdicted (slowed, deterred or stopped) and that up to fifteen thousand (15,000) airborne human antigen plumes may begin to expand and become available to gradually immunize humans with small low impact interdictions by potentially cumulative immune system boosters.

The instantaneous level of disinfection in an indoor protected space may be typically set to yield disinfection outcomes at or above 6 Log which, in the use cases described herein, implies that, considered in, for example, (2) second disinfection intervals, an air mass containing one million (1,000,000) infectious particles such as Covid 19 virus particles is reduced to an air mass containing one (1) infectious particle such as one (1) Covid 19 particle. Higher and lower log settings are feasible and practical.

In this example, the airborne "passive inoculation" effect occurs automatically as the 6 Log air-handling technologies interdict, disable and disinfect the remaining 999,999 particles thus converting some portion of these formerly infectious particles into antigens that may enable human immune systems to recognize and react to the same risk if it occurs again in the future. The technologies are extremely fast and may be regarded as dependably and overwhelmingly reliable over decades of usage. The incoming biological pathogens and allergens may be typically exhaled into the protected space by human vectors as the primary originating sources in the use cases described herein. A similar use case pertaining to other air breathing creatures is claimed but not separately described herein.

The overwhelming optical/light-based disinfection power over time of the Present Invention applies to Covid 19 variants, to expected new "superbugs" and to virtually all known airborne biological agents of potentially contagious human diseases. Thus, via applications of the present invention, the worldwide potential for human disease may be substantially reduced along with reduction of potential for deliberate large scale bio terror warfare, including covert efforts.

The breathable air in the scalable indoor protected spaces is set and controlled by the 24/7/365 operation of the systems to constantly remain below human infectious disease transmissibility levels according to industry standards wherever and whenever the protective installation or current use case is designed, installed and maintained properly.

Process Patent Attributes: The core systems of the present invention are managed by human attendants to coordinate the instances and combinations of both core and ancillary air-handling devices and selectable, attachable and detachable extensions of said core air-handling devices that may, from time to time, be connected and controlled by the circumstance of connection or non-connection of the system to said core air-handling devices in a multiplicity of combinations wherein said combinations may add to, subtract from or enhance the original systemic functionalities and outcomes of usage of the core air-handling devices for disinfection purposes and for other human and animal healthcare purposes as stipulated by the suppliers and/or end users of the present Invention including multiple categories of potentially cumulative enhancements to the human immune systems of persons within the protected spaces. The present invention protects all persons equally within the cited exemplary college and DOD settings without discrimination. For example, performance described herein with respect to DOD mess halls and college dining room could be equally applied to homeless food centers or migrant shelters anywhere on the planet.

When the ancillary air-handling devices and selectable, attachable and detachable extensions of said ancillary air-handling devices such as cleaning and disinfecting hand-operated or robotic vacuums or air propellers are in use, the typical systems configuration may be to outfit the hand-operated or robotic vacuums with removable filters that capture pollutants, and contaminants such as pollen or mildew, as examples, and selectively remove them from the relevant breathable air streams. All such vacuum type ancillary air-handling devices may discharge some or all of the residues of their vacuumed relevant breathable air streams into the enclosed air circulation feed lines of the systems such as pipes and ducts for ensuing air disinfection and for other potential healthcare and commercial usages.

A claimed potential healthcare and commercial usage is to collect, sequester and deliver or use antigens and other byproducts created by the present invention as feedstock for the production or processing of pharmaceuticals and/or cosmetics and/or other commercially or scientifically valuable materials or substances.

These ancillary vacuums may be self-powered and therefore need only the proper air-handling fittings to safely feed or otherwise exchange their waste air into the systems of the core air-handling devices. These same ancillary vacuums may be used with or without filters to vacuum air and particles from bedding and fabrics and/or to feed low $CO_2$ air into protected healthcare and education spaces as examples. These same ancillary vacuums may be energized by vacuum power supplied by the Systems, Processes and Methods of the Present Invention and used with or without filters to vacuum air and particles from bedding and fabrics and/or to feed low $CO_2$ air into protected spaces and/or to feed any air controlled by the present invention at any time into other applications such as, for example, pond or standing water remediation by cleaning and maintenance via supply of purified air to prevent build up of fungi and toxins in said pond or standing water after weather disasters such as hurricanes Sandy and Katrina. Emergence of mold and mildew colonies may also be interdicted at great benefit soon after natural disasters.

Method And System Patent Attributes: The Present Invention delivers scalable Methods to interdict i.e., slow, deter, stop, capture, kill, disable or otherwise deactivate pathogenic and allergenic organisms such as bacteria, fungi, viruses and volatile organic compounds and other pollutants and/or contaminants that are present from time to time in the air streams that are handled and controlled within the basic air-handling devices and extensions to said methods that, at the option of the systems end user, may be coupled or decoupled to and from additional methods, processes, systems, ducts, pipes, fans, propellers and chambers of the core and non-core air-handling devices of the present invention in a fashion and manner that increases the commercial, technical, healthcare or social value proposition of the primary processes, methods and systems as described herein. In a hospital setting, these advantages are expected to deliver financial savings 24×7×365.

Daily all-in analyses of savings are expected to document 2×-3× cost savings as a financial byproduct of the present invention. Everyday hospital-wide disease risk reduction and revolutionary personal and peer group health status improvement may benefit the psychology and quantifiable realities of attracting and maintaining healthcare staff. In addition, patient preferences for the claimed healthcare environments as the cleanest and healthiest breathable air available are likely to evolve. It is therefore reasonably predictable that the current exodus of healthcare professionals will reverse as healthcare workers happily return to the world and work that they love. Patients may also begin to regard hospitals as especially safe spaces.

Definitions: normal reductions of social distancing are defined as cases wherein continuous air circulation within indoor protected spaces and disinfection provided to persons and populations protected and served by the Processes, Methods and Systems of the present Invention sufficiently reduce the risks of person to person transmissibility of agents of contagious biological diseases to levels that, for example, replicate or improve prior normal social distancing spacing of patrons within a restaurant or bar setting in a manner that may become acceptable to health authorities. Examples of said normal historical spacing of patrons that are acceptable to health authorities may achieved by representative living proofs that are confirmed in sensible graduated steps with resultant actual disinfection levels confirmed by approved laboratories.

Referring now in detail to the drawings and in particular FIG. 1, there is shown an embodiment of a continuous disinfection system or device 10 according to the invention. A housing 12 contains all necessary hardware, software and disinfecting systems, requiring only electrical mains power. The housing can be flexibly sized and configured for various installations. In general, housing 12 includes one section for lamp drive access 60 and lamp and a general access port 62. All maintenance tasks can be performed via access 60 and port 62. Descriptions of hardware/software controls, communication protocols, sensors and other basic features found on air handlers and filtration systems may be found in my earlier U.S. Pat. No. 9,675,726 entitled SCALABLE AIRBORNE PATHOGEN REMOVAL SYSTEM, the contents of which are incorporated herein by reference thereto. The other section of the housing comprises a treatment chamber 20 which contains the source of UV radiation. The treatment chamber is sealed against tampering and generally inaccessible. The only breach of the seal is for one or more air intakes 14 and one or more air outputs 16. When configured as a rectangular cube, housing 20 includes a top wall 20*t*, a bottom wall 20*b*, a left side wall 20*w* and a right side wall 20*r*.

The interdicted air may contain continuously changing combinations of disinfection and air-cleansing targets including but not limited to pathogenic and allergenic airborne organisms such as bacteria, viruses and fungi along with volatile organic compounds and other pollutants and/or contaminants that may, from time to time, also be present in the air and/or on the surfaces, furniture and furnishings.

The airspace is treated by drawing air in through the air intake 14 into treatment chamber 20 having inner boundary walls (20*t*, 20*b*, 20*w*, 20*r*) that protectively surround a source of ultraviolet irradiance. An accessible filter tray 14*f* is provided to accommodate replaceable filters 52. Housing 12 has a volume within the boundary walls measured on a basis of a unit size of 1 cubic foot. An airflow management system is installed on one or more of the inner boundary walls that provides, amongst other functions, a narrow exposure slot 42*s* adjacent the source of UV irradiance. The exposure slot is dimensioned based on the UV irradiance source power to insure a high dose of disinfecting irradiance for all air passing therethrough. In a practical embodiment, the exposure slot has a cross-sectional area that receives at least 20 kWatts/m2. An air motivator, like a fan or blower, draws air from the air space through the treatment chamber 20. The air flow management system directs air through the exposure slot to provide all drawn air with a minimum exposure time of at least 250 milliseconds, for example at least 360 milliseconds of dwell time. Two or more exposure slots may be provided in serial or parallel depending on the rated capacity of the device, and its overall configuration. The minimum exposure will provide treated air with at least 99.99% of pathogens eradicated, and in several embodiments of the device, higher rates above 99.999% of pathogens eradicated. The air flow management system further functions to maintain a throughput of 100 units of air per minute, for example 120 units (cubic feet) of air per minute. Treated air is then expelled from air outputs 16 and return via ducts to the airspace. For systems large enough for two or more air inputs/outputs, the location of the outputs may be staggered with respect to the inputs. That is, each input does not necessarily have a corresponding aligned output in the X direction. In the illustrated embodiment, one input is aligned with one output adjacent the left wall 20*w* and one input is aligned with one output adjacent the right wall 20*r*. The remaining ducts comprise four central inputs and three staggered outputs. Accordingly, input and output ducts may be aligned or staggered. Some input ducts may be aligned with output ducts where boundary conditions provide sufficient turbulence to prevent laminar flow from input to output, for example, adjacent a side wall where the air flow management system terminates. Other inputs are misaligned with outputs to force air flow in a lateral direction, thereby disrupting laminar flow and increasing mixing for more complete irradiance.

All of the air once within and traveling through said channels and chambers is exposed to certain UVC wavelengths between 253.7 and 275 nm that deactivate the covalent bonds of said pathogenic organisms' DNA and also negatively affects RNA to an extreme degree wherein said exposure is set to achieve disinfection outcomes at or above 6 Log which, in this use case, implies that, considered in two (2) second disinfection intervals, an air mass containing one million (1,000,000) infectious particles such as Covid 19 virus particles is reduced to an air mass containing one (1) or less infectious particle such as Covid 19. The same overwhelming optical disinfection power over time applies to Covid 19 variants, expected new "superbugs" and virtually all known airborne biological agents of potentially contagious human diseases. Said 6 Log disinfected air is thereafter propelled continuously 24/7/365 into the protected space or spaces for purposes of dilution and for additional purposes that further reduce the abilities of targeted biological pathogens and allergens to achieve infectious concentrations within the protected spaces.

This mentioned optical energy exposure is of the intensity, length In time and degree that the pathogenic DNA and to a great extent RNA, of the airborne pathogens and allergens that travel in the air or by any other method, through said device will be deactivated up to and past a six-log reduction in volume in most cases.

Indoor and/or outside air is directed by proprietary combinations of pushing and/or pulling fans or other air movers and by mechanical devices and by configurations that move, direct, homogenize and diffuse air via air-handling and mixing baffles and architectures into around and through chambers of varying shapes and sizes that may be contained within additional chambers of varying shapes and sizes wherein said multi chamber or chamber within chamber architectures may be both for structural reasons and/or for Process reasons, and/or for outcome reasons, including conformance with usage of any configuration of said air-handling systems to be combined with facades, furniture and furnishings to produce specific purified air, disinfected air, healthcare attributes, employee productivity gains and/or novel processes and methods and configurations of furniture and furnishings to control appearances and heating and air-conditioning energy costs and, as a by-product of said configurations developed to produce environmentally meaningful and commercially valuable reductions of greenhouse gas emissions and/or to beneficially reduce the need for social distancing in situations wherein reductions to historically normal social distancing practices are desirable.

Certain features are explained and defined with respect to an X-Y plane which typically represents a central location within the treatment chamber. The X-Y plane typically intersects the side walls and may bisect the chamber or pass through elongated UV light bulbs. The X-Y plane is typically parallel to the top and bottom walls may pass through some or all of the air intakes and outputs. A Z direction extends perpendicular to the X-Y plane. The top wall is located in the positive X direction, while the bottom wall is located in the negative X direction. The air flow management system varies in height as measured in the Z direction and induces turbulence to the passing air to an extent that it achieve a high Reynolds number, that is, degree of mixing. Higher turbulence is desirable to avoid clumping, tailing, trailing and shadowing of particles to maximize pathogen eradication.

The treatment chamber(s) may be installed in, on or around any manner of structure with wheels or without wheels and/or be either airborne, fixed, mobile, portable, submersible and/or underground applications. Each said structure manifesting usage of claims of the Present Invention may serve a different goal of the overall disinfection value proposition(s) of the Present Invention. The device may have both internal and/or external onboard or airborne, rechargeable and/or ground based energy sources for the various operating needs of the device. The device may be combined with any ancillary device that when combined with, and/or used in conjunction with, scalable combinations of other ancillary devices and/or chambers, may reduce and/or eliminate volatile organic compounds (VOC's) and other pollutants and/or contaminants that may, from time to time, be present in the air and/or on the surfaces that are subjects of the Methods and Extended Methods of the present Invention. The device may have extendable or retractable methodologies and devices for specific targeted external UVC germicidal irradiation intentions, services and routines specifically including methodologies and devices that vacuum surfaces and deliver the vacuumed organisms and matter to the air-handling devices for subsequent disinfection, destruction and disposal and/or for enhancement of the performance of human immune system(s). Importantly, in accordance with the claims of the present invention, the utilization of said chambers and their extensions and appurtenances may be implemented in a fashion wherein the air-handling technology does not introduce anything new into the breathable air or onto the surfaces that are within the direct space that is served by the air-handling devices.

Instead, the present Invention vacuums-in undesirable biological agents and other micron and sub micron pollutants, contaminants and irritants thus removing them from the captured air-streams and, after disabling and disinfection of the captured biological pathogens and allergens, returns the same air and purified outside low CO2 air to the protected space. Thus, to the extent possible within the purpose contexts of the present invention, does not introduce anything new into the normal breathable air in the indoor protected spaces.

The device may have extendable and retractable methodologies for specific targeted external UVC germicidal irradiation intentions, services, routines and/or any other purposes. These disinfection devices may be collaborative robots, or "Cobots" and must comply and/or follow all regulatory and design methods pertinent.—see—ISO regulatory guidance. The device may be combined/conjoined or working in conjunction with any living plant or vegetative organism of the kinds exemplified by trees, shrubs, herbs, grasses, ferns and mosses typically growing in permanent sites, absorbing water and inorganic substances through its roots, leaves and stems and synthesizing nutrients in its leaves by photosynthesis using the green pigment, chlorophyll. The device may have extendable, portable and/or replaceable methodologies for specific external air movement intentions. The device may be equipped with external and/or internal communications wired and wireless methodologies for collection, reporting and storage of data that is specifically related to the workloads and performance of the System(s).

The treatment chambers may have both external and/or internal controls and/or methodologies for detection of fixed and/or moving living animals or humans of any size either indoors and/or outdoors. The treatment chambers may have both external and/or internal methodologies for communicating, handling, maintenance and/or movement purposes. The treatment chambers may be portable with wheels, skids, skis, have airborne capabilities, and be scalable in size and shape for varying intents and purposes. The treatment chambers shall have extendable and retractable apparatus for the purpose of targeting and/or moving amongst nonspecific size and shape areas that may contain animals, humans and varying targets requiring an exacting and/or global delivery of disinfected air. A feature for healthcare and commercial usage is to collect, sequester and deliver or use antigens and other byproducts created by the present invention as feedstock for the production or processing of pharmaceuticals and/or cosmetics and/or other commercially or scientifically valuable materials or substances. Because the present invention uses only high energy light in unique proprietary ways to eradicate and/or disable biological pathogens and allergens, the resultant antigens are free of any non-native residue that is otherwise a normal unwanted artifact of known competing antigen production processes. This is an important competitive advantage because, for example, vaccines containing production residues of warp speed production processes are killing and otherwise harming patients receiving the warp speed vaccine injections, because of the residues. The light used to create the antigens claimed in the present invention dissipates immediately and therefore cannot remain as a contaminating residue.

Figure 3:
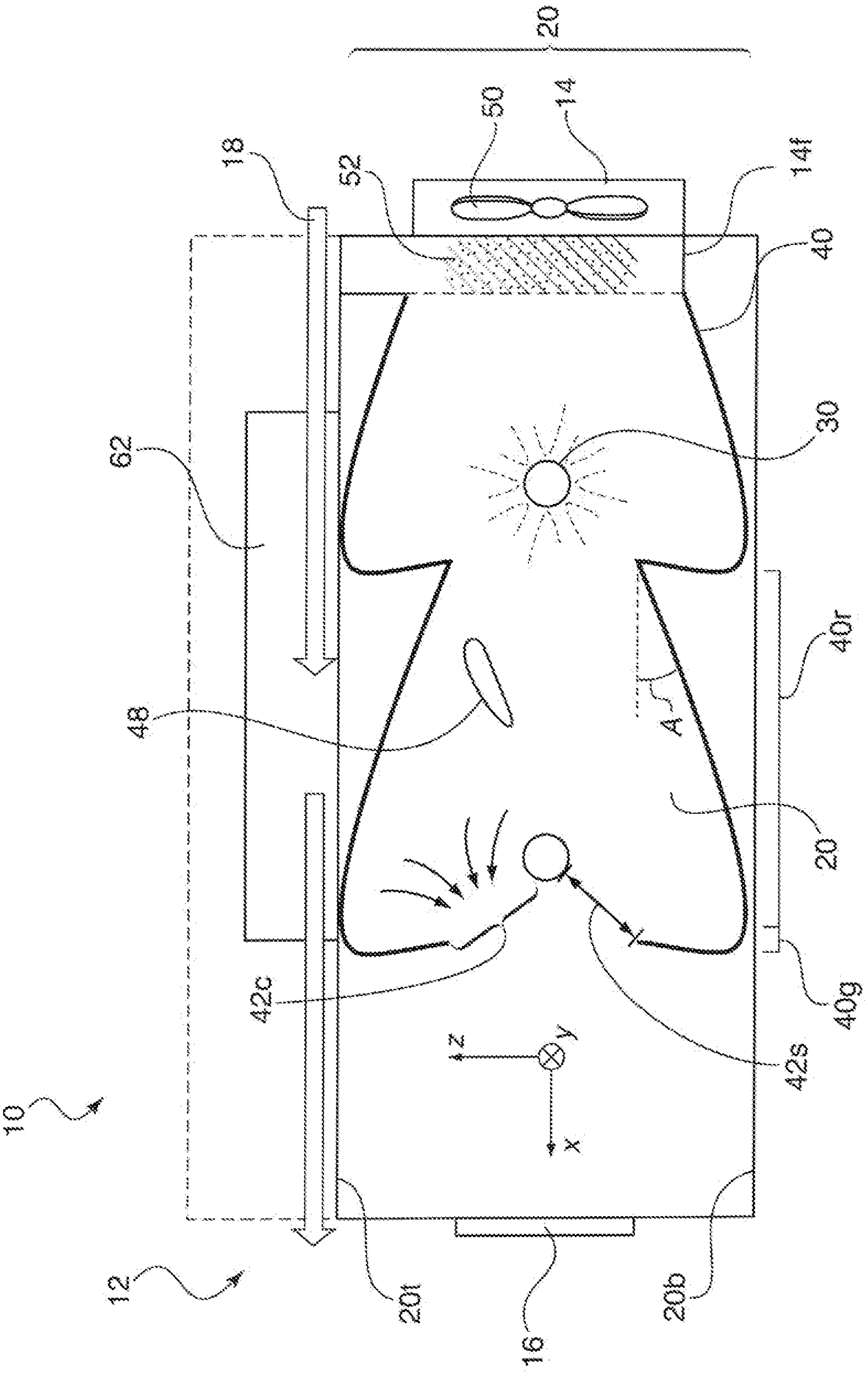
FIG. 3 is a cross-sectional view taken along the line III-III from FIGS. 1 and 2.

In those cases where the invention is purposed in part toward global, regional or hyperlocal human immune system boosting or other types of human healthcare improvements, including the fundamental disinfection purposes of the invention, it is feasible that, in a use case such as for example a large DOD mess hall feeding thousands of soldiers, one hundred (100) different types of living airborne biological infectious agents may be entering and re-entering the protected space simultaneously via human vectors. In this example, due to the fact that the present invention operates at optoelectronic speeds and processes viruses, bacteria and fungi sized in the micro, nano and smaller ranges; and, due to the fact that all of the breathable air in the protected spaces is constantly recirculated and subjected to optical irradiation so powerful as to produce six log or greater numerical reductions of infectious populations of viruses, bacteria, and fungi, important new public health outcomes are feasible, practical and available. Thus novel capabilities to convert massive numbers of pathogens to antigens within any protected spaces is a claim of the present invention The device includes advanced capabilities to constantly circulate and recirculate massive numbers of pathogens and allergens through the device of the present invention. An exemplary configuration for the circulating and recirculating capabilities are shown in FIG. 3. Starting at the right side of the drawing and proceeding to the left side in a downstream direction, there is provided a fan 50 set within one air intake or duct 14. A filter 52 disposed with tray **14*f* shields UV irradiance from exiting the treatment chamber and removes dust, particulates and foreign matter from entering the treatment chamber where they can shield pathogens from irradiance, cloud the UV lamps and generally deteriorate the components. A pair of lamps 30 is located on the X-Y plane. Each lamp has a corresponding section of the air flow management system 40. Starting at the filter, or air intake, the air flow management system comprises a ramp section 40*r* and a gate section 40*g*. The ramp section 40*r* originates upstream of the lamp and slopes toward the inner boundary wall. In the case of a constant slope, the angle A is measured with respect to the X-Y plane. Depending on the configuration of the treatment chamber, the angle can vary between 0-90 degrees, where slopes for a rectangularly dimensioned treatment chamber as illustrated are in the range of 10-40 degrees. The ramp passes the lamp and is closest to the inner boundary wall at a location downstream of the lamp. The gate section 40*g* includes a terminal end that narrows the cross-sectional area of the treatment chamber (in the vertical or Z direction) by 30 to 70 percent, ideally 40 to 60 percent to provide the exposure slot 42*s***. The gate section randomizes air flow away from the inner boundary wall toward the UV lamp. The power of the UV lamp and the dimensions of the exposure slot are selected to provide 20-35 k Watts/m2 across the entirety of the exposure slot. In the case of a tubular UV lamp, bulb or LED, the lamp extends in a Y direction, into the page, though 90-100% of the treatment chamber, preferably 95-100%. That is most of the distance between the left wall and the right wall. The lamp emits UVC irradiance that is UV in the range of 253.7 and 275 nm, inclusive.

The gate section **40*g* extends away from the inner boundary wall in a generally perpendicular direction and creates a choke point 42***c*. The choke point is the aerodynamic equivalent of the photooptical exposure slot. The choke point 42*c* increases the velocity of the air passing in the downstream direction to maintain throughput. The Bernoulli Principle is used to realize the best UVC photooptical dosage outcomes to the airflow. A fixed volume of air that passes through a narrowed opening increases in velocity according to the Bernoulli Principle. In the device, the choke point 42*c* operates as the narrow opening.

The ramp section 40*r* and the gate section 40*g* are formed from a continuous ribbon of polished material having a reflectivity of at least 70% and ideally at least 80%. The continuous ribbon could be formed from polished metal or coated polymer, for example. The ramp section 40*r* smoothly curves at is transitions to the gate section 40*g*. The gate deflects, in the minus X direction, a distance equal to about 10-20% of its length toward the UV lamp 30 as it approaches the choke point 42*c*. The power of the UV lamp and the reflectivity of the continuous ribbon are selected to provide between 20-35 kWatts/m2 across the entirety of the exposure slot 42*s*. Air entering the ramp section hugs the continuous ribbon according to the Coanda Effect. Air encountering a discontinuity at the end of the gate section at the choke point becomes turbulent in the vicinity of the UV source to increase dwell time and mixing to provide a 6 log reduction in pathogens in the exposed air. In summary, the Coanda Effect is used to achieve maximum UVC photooptical disinfection outcomes to the airflow. Air hugs the continuous ribbon according to the Coanda Effect until it encounters a stronger force. The discontinuity at the end of the gate section causes the air to break free of the gate section and swirl around freely, since the aerodynamic force in the downward direction and the 90+ degree angle at the discontinuity prevents further flow along the surface of the continuous ribbon. Novel physical concentrated capabilities are provided to disinfect and disable massive numbers of random pathogens present in any protected space as a deliberate mechanism to create massive, aerosolized inoculation instance events and continuums are a claim of the invention. Novel use of the Least Squares theory, a mathematical technique that allows the analyst to determine the best way of fitting a curve on top of a chart of data points, coupled with a proprietary calculated photoelectric distance to maximize dosage throughout the internal irradiance chamber(s). This unique combination of mathematical tools shall aid in the creation of the best possible deactivation outcome of microorganisms.

Carbon Dioxide ($CO_2$) Diffusion may be achieved by locating and otherwise sourcing some of the devices designated return air flows in areas that, by design and purpose, have lower resident $CO_2$ levels than other parts of the building(s). Some areas in most buildings have locations where full-time occupancy is sharply lower, on average, than other places of occupancy within the building. Areas like halls, stair wells, areas near to and around the same, closet (s), designated storage areas, landings and lobbies as well as the unused areas above ceilings generally harbor much lower $CO_2$ levels than anywhere else in the building. The device may include supplemental air intakes to draw air from sources separate from the main airspace designated for treatment. The supplemental air intakes may be freely located on any wall of the housing. As with the primary air intakes, the supplemental air intakes are fitted with replaceable air filters to limit particulate matter, debris and foreign objects from entering the treatment chamber. FIG. 3 shows two possible locations for supplemental air intakes 14*s*. Automatic $CO_2$ monitors may be located throughout the installed areas and will be connected to various system duct apparatus to open and close various duct gates to balance the $CO_2$ levels at the lowest possible levels within the various installed locations.

Mathematical computer verification is utilized as authentication and proof that the claimed dosages of UVC disinfection power levels are delivered both on the spot and in the moment. The mathematical computer verification UVC dosage metrics and program have been performed by a program supplied by the manufacturer of the UVC lamps utilized within said disinfection chambers. The disinfection chamber is designed to take maximum advantage of the specific UVC wavelength (253.7 nm) that has been proven in science to deactivate bacterial, fungal and viral DNA to beyond deactivation levels without survival. The mathematical computer mentioned above served as a design tool of the disinfection chamber of said invention. The inventor(s), using output from said computer, developed a proprietary design that extended and multiplied, by degrees, the deactivation abilities to beyond a level from which no recovery may be expected. No recovery is meant to mean that less then 1 PPM (parts per million) microorganism could survive for any infectious or duplicative purpose. For medium size disinfection systems, air drawn through the treatment chamber is directed through one or more stages that are serially-aligned in the downstream direction. Each stage comprises a symmetrically increasing cross-sectional area that originates adjacent to, or in contact with a intake, fan or filter. The increasing cross-sectional area then extends past the UV source followed by a symmetrical reduction in cross-sectional area of 30-70%. The contour profile of the continuous ribbon is conjunction with a filtered volume of air drawn in to the treatment chamber mechanically balances induced turbulence for extended dwell time with throughput as a function of unit size. While the location and reflectivity of the continuous ribbon in conjunction with a power output and configuration of the UV source photooptically maximize the irradiance of all particles. The symmetrically increasing cross-sectional area is represented by lower ramp section 40*r* mounted on bottom wall 20*b* and its mirror image mounted on top wall 20*t*. In the illustrated embodiment, symmetry can be found with respect to the rectangular treatment chamber 20 and the X-Y central plane that contains the UV lamps. In other applications, symmetry may be found with respect to only one of these references.

Figure 2:
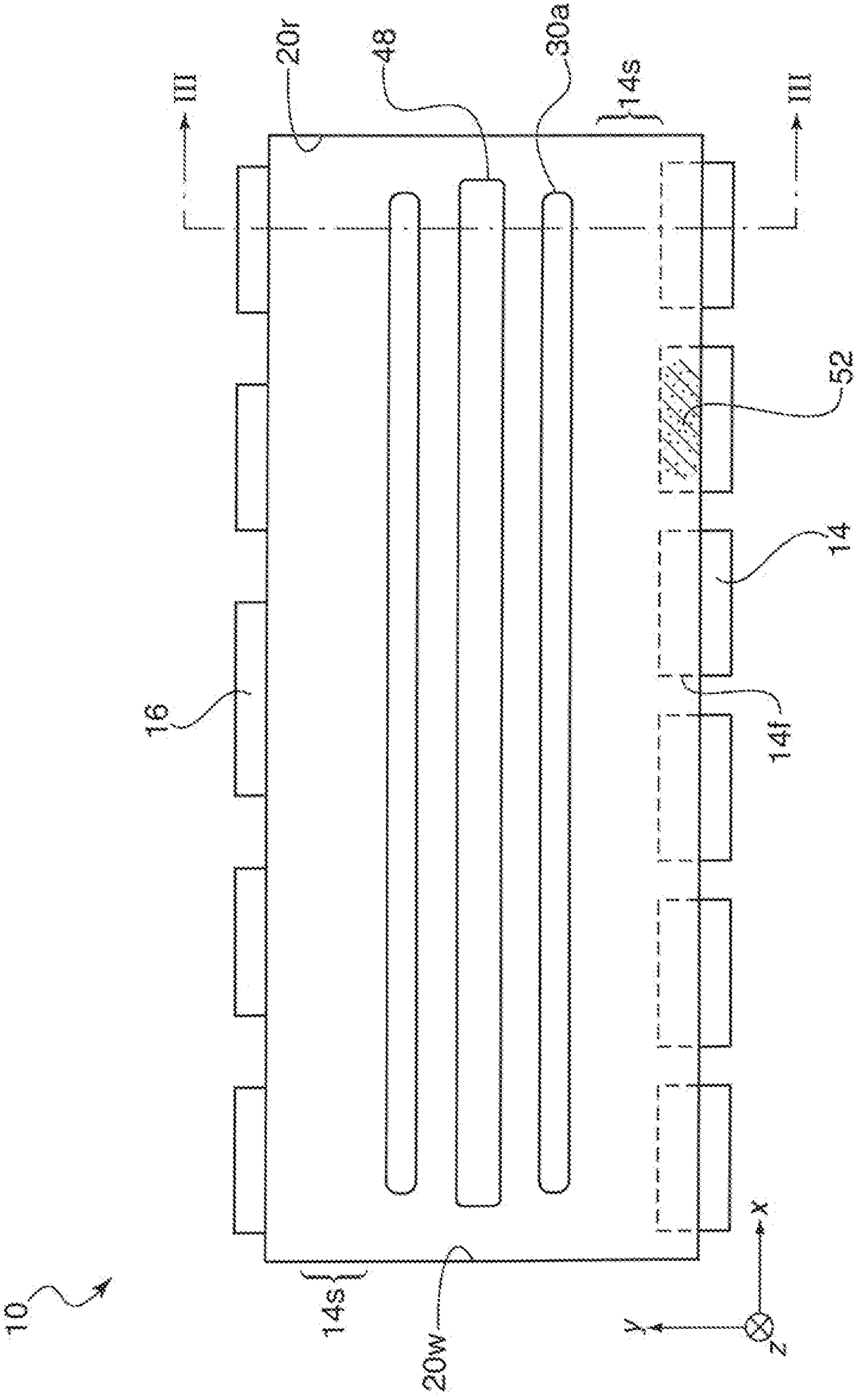
FIG. 2 is a top view of the device illustrating exemplary placement of UV bulbs and a strake.

In summary, the present invention may use various known or new air-handling methods, processes and sub systems that, when used to implement the present invention in novel ways, via application of ultraviolet germicidal irradiation (UVGI) and/or other forms of purposed energy emissions potentially including narrow and multi spectral light emissions; e-beams; avalanche dump laser light emissions, x rays, LED's and ultra sound; among others to achieve a sequence of physical events that, in whole or in part may Interdict (slow, deter or stop), disable and/or kill airborne biological agents of potential infections, contagions and pandemics. The invention utilizes UVGI also referred to a radiation in the UVC range having a wavelength of 253.7 to 275 nm, inclusive. Any source of such UVC now in existence or developed in the future may be utilized with the inventive device. In a practical embodiment, longitudinally-extending UVC lamps 30*a* as shown in FIG. 2 have been employed. This includes various forms of lamps, bulbs and LED sources of UVC. Depending on the intended capacity of the device, one or more UVC lamps may be installed in a treatment chamber. For a medium sized device as illustrated, two longitudinally-extending lamps 30*c* are aligned in the Y direction. The lamps extend perpendicular from right wall 20*r* to left wall 20*w*, for example, 90-100% of the distance between the left and right wall, preferably between 95-100% of the distance between the left and right side walls. The longitudinal lamps are parallel to each other within the X-Y plane. Other lamps may be provided in serial or parallel arrangements to accommodate housings of different sizes and configurations. A continuous ribbon is provided for each UVC lamp. In other words, each UVC lamp is placed within one continuous ribbon, so that the ribbon can manage air flow and dwell time around the associated lamp. In the case of serial lamps, and serial ribbons, the terminating gate section of the first ribbon is coupled to the originating ramp section of the second ribbon, as shown in FIG. 3.

When two or more longitudinal lamps are disposed serially, a strake 48 is provided for each pair of lamps. A strake is analogously shaped like an airplane wing without the tapering. In the invention, the strake has a lower flat surface and a slightly curved upper surface. This cross-sectional shape is shown in FIG. 3. The upper surface may be symmetrically shaped on the left and right sides. Alternatively, the left side may have a different dome contour than the right side, as illustrated with the right side being thicker than the left side. The strake is aligned approximately midway in the X direction between its respective pair of lamps as shown in FIG. 2 to further increase the air's turbulence. The combination of a lower flat side facing the lamps, and a slightly curved upper surface maximize the production of mini eddies. Where three or more longitudinal lamps are disposed serially, the two or more strakes are disposes alternately above and below the X-Y plane.

The features of the air flow management system may be summarized as including a first continuous ribbon extending partially across one of the inner boundary walls having a height above the X-Y plane measured in the +Z direction. Where the height of the first continuous ribbon varies in the X direction while maintaining a constant height in the Y direction. A second continuous ribbon extends partially across an opposite one of the inner boundary walls having a height measured in the −Z direction. The height of the second continuous ribbon varies in the X direction while maintaining a constant height in the Y direction.

The continuous ribbon comprises a ribbed panel that extends across 80-90% of the length one of the inner boundary walls measured in the Y direction. An edge of a ribbed panel provides a discontinuity to increase the turbulence of the air flow at a side wall of the treatment chamber. The continuous ribbon induces turbulence characterized by a high Reynolds number, preferably an Re of between 4,000 and 5,000.

The Reynold's Number (Re) is calculated by the following formula.

$$Re_D = \frac{\rho VD}{\mu} = \frac{VD}{\nu}$$

An Re less than 2000 is considered low velocity, fluid motion generally in a straight line with virtually no mixing between layers. In contrast, an Re greater than 4,000 is considered high velocity, in which particles within the fluid experience irregular motion.

The present invention also asserts new claims to the scalability of certain sequences and power levels of same or similar known energy emitters that may also continue to be linked to air circulation and air recirculation processes that disrupt and/or prevent formation of infectious concentrations of pathogens and allergens thus generally protecting air breathing creatures. Advances of the present invention elevate the interdiction performance to a level at which the airborne spreading progress of a contagion among humans can be stopped within a protected indoor space of the invention. Each "stopped" location is thereby eliminated as a possible disease super spreader node in a contagious network. Furthermore each "stopped" location becomes a potential herd immunity microcell.

Furthermore, implementation of the present invention, with or without the prior known air-handling methods, may include a multiplicity of new sequences and cycles that disable, kill, eradicate and/or interdict (slow, deter or stop) formations of infectious concentrations of disease caused by viruses, bacteria and fungi, along with many additional pollutants and contaminants. Advances of the present invention can elevate the interdiction performance to a level at which the airborne spreading progress of a contagion can be stopped within a protected indoor space of the invention. Human immune systems and immune systems of other air breathing creatures are beneficially activated by a new class of antigens produced by the present Invention wherein said antigens have unique readability and information transfer capabilities versus other types of antigens that are not created via the unique and novel workings of the present invention. Said uniqueness is, in part, a direct result of the fact that light, which is used to create the antigens, does not leave a residue. In contrast, antigens that are created using chemicals or biological intermediaries may leave residues that diminish readability and information transfer capabilities of the subject antigens. The outcome differences enabled by the present invention are crisper, cleaner, more reliable antigens that convey information to be converted by human immune systems into antibodies including molecules such as amino acids and cells that, in turn, guide the workings of human immune systems.

Antigens are automatically mass produced by each protected human body in reaction to the first potentially infectious human contact within relevant air streams of potentially airborne infectious biological agents and may thereafter be exhaled as antigens to the benefit of all occupants of the protected space. An important feature of the claim is that the human who formerly exhaled potentially infectious pathogens is now exhaling potentially protective antigens. The workings of the invention converted the pathogens into antigens. Production of each type of said antigens is automatically stopped or paused in reaction to the first disappearance of corresponding pathogens within relevant air streams of potentially airborne infectious biological agents. The systems level architecture, sequencing and energy dynamics of the applicable systems, processes and methods constitutes the overriding unifying claim that enables the present invention to achieve new levels of reliable disinfection in interior spaces. The present invention achieves highly focused and concentrated applications of Ultraviolet Germicidal Irradiation (UVGI) to uniquely consolidated and confined target air streams at high speeds and in large volumes thereby achieving and maintaining chosen levels of disinfection of breathable air that, thereafter, is constantly recirculated throughout the protected space(s). The relationship between irradiation from a radiation source and irradiance should be noted. Irradiance is the flux of radiant energy per unit area (normal to the direction of flow of radiant energy though a medium). Irradiance is also, or alternatively, defined as the density of radiation incident on a given surface usually expresses in watts per square centimeter of square meter. In the present invention, irradiance is the dosage calculation of flux, distance, time and UVC wattage which is calculated internally to deliver the highest possible UVC dosage in wattage/m2 to inactivate (breaking the covalent bond) the DNA of microorganisms.

The automatic Aerosolized Immunization workings of the invention can simultaneously or sequentially achieve a relevant level of sustainable immunizations of a multiplicity of potential infections inclusive of approximately 400 families of viruses, bacteria and fungi and their thousands of mutating offspring and variants. A contagious airborne pathogen that first infects humans in a new location simultaneously and automatically stimulates an aerosolized immunization response in protected spaces. Resultant antigens may be harvested immediately as desirable feedstock for new traditional vaccines. The present invention may disable or reduce infectious potentials of future contagions and pandemics because of the ability to exchange higher quality antigen information with the astounding immune system benefits of somatic hypermutation which may control an orderly system of one quintillion antibodies per human.

Having described preferred embodiments (which are intended to be illustrative and not limiting) for components, configurations and relative capacities, it is noted that modifications and variations can be made by persons skilled in the art in light of the above teachings. For example, the type and number of bulbs can vary depending on the required configuration for the housing and amount of airspace to be treated. As the size and dimensions of the housing vary, the air flow management system can be flexibly designed to provide one stage per bulb. While various embodiments may be constructed, the key is to balance the variables of disinfection to always provide treated air with at least 99.99% of pathogens eradicated. It is therefore to be understood that changes may be made in the particular embodiments of the invention disclosed which are within the scope and spirit of the invention.

What is claimed is:

1. A continuous disinfection device for removing pathogens from an airspace comprising:

a housing having an air intake and an air output;

a treatment chamber having inner boundary walls protectively surrounding a source of ultraviolet (UVC) irradiance within said housing and having a volume within the boundary walls measured on a basis of a unit, wherein the unit is 1 cubic foot;

an air flow management system disposed between the inner boundary walls and the source of ultraviolet irradiance to provide an exposure slot having a cross-sectional area receiving at least 20 kWatts/m2, wherein the air flow management system includes a ramp section that originates upstream from the source of ultraviolet irradiance spaced from the inner boundary wall and slopes toward the inner boundary wall, wherein the ramp section is closest to the inner boundary wall at a location that is downstream of the source of ultraviolet irradiance; and an air motivator configured to draw air from the airspace into the air intake through the treatment chamber in a downstream direction and expel treated air out of the air output back to the airspace, wherein the cross-sectional area of the exposure slot is configured and dimensioned to provide all drawn air with at least 360 milliseconds of dwell time within the exposure slot to produce treated air with at least 99.99% of pathogens eradicated while maintaining a continuous throughput of about 120 cubic feet of air per minute for each unit drawn into and expelled out of the disinfection device.

2. The device according to claim 1, wherein the treatment chamber includes an X-Y central plane where air passes through the treatment chamber in a downstream X direction, wherein the passing air encounters the air flow management system that varies in height as measured in a Z direction perpendicular to the X-Y central plane to induce turbulence characterized by a high Reynolds number so that clumping, grouping, tailing, trailing and shadowing is avoided to maximize pathogen eradication.

3. The device according to claim 2, wherein the air flow management system further includes a gate section with a terminal end which narrows the cross-sectional area of the treatment chamber by 40 to 60 percent to direct a randomized air flow away from the inner boundary wall toward the source of ultraviolet irradiance.

4. The device according to claim 3, wherein the source of ultraviolet irradiance generates between 20-35 kWatts/m2 across the entirety of the exposure slot and comprises a longitudinally-extending ultraviolet lamp, bulb, or LED oriented parallel to the terminal end of the gate section through 95-100% of the treatment chamber emitting irradiance in the range of 253.7 and 275 nm, inclusive.

5. The device according to claim 4, wherein the gate section extends away from the inner boundary wall in a generally perpendicular direction and creates a choke point that increases the velocity of air passing through the choke point according to the Bernoulli Principle.

6. The device according to claim 5, wherein the gate section and the ramp section are formed from a continuous ribbon having a reflectivity of at least 80%, wherein the source of ultraviolet irradiance and the reflectivity of the continuous ribbon are selected to provide between 20-35 kWatts/m2, on average, across the entirety of the exposure slot.

7. The device according to claim 6, wherein ramp section smoothly curves as it transitions in to the gate section, and wherein the gate section deflects a distance equal to 10-20% of its length in the upstream direction toward the source of ultraviolet irradiance as it approaches the choke point.

8. The device according to claim 7, wherein the air flow management system directs air drawn in to the treatment chamber through one or more stages serially-aligned in the downstream direction, where each stage comprises a symmetrically increasing cross-sectional area that extends past the source of ultraviolet irradiance followed by a symmetrical reduction in cross-sectional area of 30-70%, whereby a contour profile of the continuous ribbon in conjunction with a filtered volume of air drawn in to the treatment chamber mechanically balances induced turbulence for extended dwell time with throughput as a function of unit size while the location and reflectivity of the continuous ribbon in conjunction with a power output and configuration of the UV source photooptically maximize the irradiance of all particles.

9. The device according to claim 8, wherein air entering the ramp section hugs the continuous ribbon according to the Coanda Effect; air encountering a discontinuity at an end of the gate section at the choke point becomes turbulent in the vicinity of the source of ultraviolet irradiance to increase dwell time and mixing to provide a 6 log reduction of pathogens in the exposed air.

10. The device according to claim 9, wherein the source of ultraviolet (UVC) irradiance comprises two or more longitudinally-extending ultraviolet lamps, bulbs or LEDs aligned in the Y direction and arranged parallel to each other within the X-Y plane and wherein a continuous ribbon is provided for each source of ultraviolet irradiance, with the gate section of one ribbon coupled to the ramp section of a further ribbon.

11. The device according to claim 10, further comprising a strake for each adjacent pair of longitudinally-extending ultraviolet lamp, bulb, or LED wherein two or more strakes are disposed alternately above and below the X-Y plane with each strake aligned approximately midway in the X direction between its respective pair of lamps or bulbs to further increase the air's turbulence, wherein each strake includes one flat side and one wing-like curved side to maximize the production of mini eddies.

12. The device according to claim 11, further comprising supplemental air intakes for drawing from sources separate from the airspace freely located on any wall of the housing and replaceable air filters on all intakes to limit particulate matter, debris and foreign objects from entering the treatment chamber.

13. The device according to claim 12, wherein the air flow management system includes a first continuous ribbon extending partially across one of the inner boundary walls having a height above the X-Y plane measured in the +Z direction, wherein the height of the first continuous ribbon varies in the X direction while maintaining a constant height in the Y direction and a second continuous ribbon extending partially across an opposite one of the inner boundary walls having a height measured in the −Z direction, wherein the height of the second continuous ribbon varies in the X direction while maintaining a constant height in the Y direction.

14. The device according to claim 13, wherein the continuous ribbon comprises a ribbed panel that extends across 80-90% of the length of one of the inner boundary walls measured in the Y direction; wherein an edge of a ribbed panel provides a discontinuity to increase the turbulence of the air flow at a side wall of the treatment chamber; wherein the continuous ribbon induces turbulence characterized by a high Reynolds number, preferably an Re of between 4,000 and 5,000.

15. A continuous disinfection device for removing pathogens from an airspace comprising:

a housing having an air intake and an air output;

a treatment chamber having inner boundary walls protectively surrounding a source of ultraviolet (UVC) irradiance within said housing and having a volume within the boundary walls measured on a basis of a unit, wherein the unit is 1 cubic foot;

an air flow management system disposed between the inner boundary walls and the source of ultraviolet irradiance to provide an exposure slot having a cross-sectional area receiving at least 20 kWatts/m2, wherein the air flow management system further includes a gate section with a terminal end which narrows the cross-sectional area of the treatment chamber by 40 to 60 percent to direct a randomized air flow away from the inner boundary wall toward the source of ultraviolet irradiance; and an air motivator configured to draw air from the airspace into the air intake through the treatment chamber in a downstream direction and expel treated air out of the air output back to the airspace, wherein the cross-sectional area of the exposure slot is configured and dimensioned to provide all drawn air with at least 360 milliseconds of dwell time within the exposure slot to produce treated air with at least 99.99% of pathogens eradicated while maintaining a continuous throughput of about 120 units of air per minute drawn into and expelled out of the disinfection device.

16. The device according to claim 15, wherein air encountering a discontinuity at the terminal end of the gate section becomes turbulent characterized by a Reynold's number (Re) between about 4,000 and 5,000 in the vicinity of the source of ultraviolet irradiance to increase dwell time and mixing to provide a 6 log reduction of pathogens in the exposed air.

17. The device according to claim 16, wherein the air flow management system includes a ramp section that originates upstream from the source of irradiance spaced from the inner boundary wall and slopes toward the inner boundary wall, wherein the ramp section is closest to the inner boundary wall at a location that is downstream of the source of ultraviolet irradiance.

18. The device according to claim 17, wherein the gate section and the ramp section are formed from a continuous ribbon having a reflectivity of at least 80%, wherein the source of ultraviolet irradiance and the reflectivity of the continuous ribbon are selected to provide between 20-35 kWatts/m2, on average, across the entirety of the exposure slot.

19. The device according to claim 18, wherein the source of ultraviolet (UVC) irradiance comprises two or more longitudinally-extending ultraviolet lamps, bulbs or LEDs and the device further includes a strake for each adjacent pair of longitudinally-extending ultraviolet lamp, bulb, or LED approximately midway between its respective pair of lamps, bulbs or LEDs to further increase the air's turbulence, wherein each strake includes one flat side and one wing-like curved side to maximize the production of mini eddies.

* * * * *